United States Patent
Duan et al.

(10) Patent No.: US 8,701,677 B2
(45) Date of Patent: Apr. 22, 2014

(54) SYSTEM AND METHOD FOR DETERMINING THE POSITION OF A REMOTE OBJECT

(75) Inventors: Xiaodong Duan, Pleasanton, CA (US); Guohua Xiao, Plano, TX (US); Xinhong Wang, San Diego, CA (US)

(73) Assignee: Ankon Technologies Co., Ltd., Wuhan (CN)

( * ) Notice: Subject to any disclaimer, the term of this patent is extended or adjusted under 35 U.S.C. 154(b) by 819 days.

(21) Appl. No.: 12/753,931

(22) Filed: Apr. 5, 2010

(65) Prior Publication Data
US 2011/0240044 A1    Oct. 6, 2011

(51) Int. Cl.
*A61B 19/00* (2006.01)
*G01R 33/02* (2006.01)
*G01R 33/025* (2006.01)

(52) U.S. Cl.
USPC .......................................... 128/899; 128/898

(58) Field of Classification Search
USPC ............... 128/899; 600/117; 702/94
See application file for complete search history.

(56) References Cited

U.S. PATENT DOCUMENTS

| 5,558,091 | A | | 9/1996 | Acker | |
|---|---|---|---|---|---|
| 5,997,473 | A | * | 12/1999 | Taniguchi et al. | 600/117 |
| 6,216,028 | B1 | | 4/2001 | Haynor | |
| 7,656,159 | B2 | * | 2/2010 | Edelstein | 324/326 |
| 7,902,820 | B2 | * | 3/2011 | Vervaeke et al. | 324/251 |
| 2004/0097803 | A1 | * | 5/2004 | Panescu | 600/424 |
| 2005/0261570 | A1 | * | 11/2005 | Mate et al. | 600/411 |
| 2008/0177178 | A1 | * | 7/2008 | Aoki et al. | 600/424 |

FOREIGN PATENT DOCUMENTS

EP    1932463 A1 *    6/2008

* cited by examiner

*Primary Examiner* — Charles A Marmor, II
*Assistant Examiner* — Thaddeus Cox
(74) *Attorney, Agent, or Firm* — Treasure IP Group, LLC (57) ABSTRACT

The invention provides methods and systems for determining the position of a remote object such as an in vivo medical device such as capsule or probe within a medical patient. The systems and methods of the invention may also be used in other enclosed environments such as fluid handling or mechanical systems. The systems and methods of the invention use one or more external magnetic sensor arrays for sensing the magnetic field of a remote object within a target area. The position of the object is determined by applying magnetic field spatial geometry characterization point analysis to evaluate the sensed magnetic field.

12 Claims, 5 Drawing Sheets

SYSTEM AND METHOD FOR DETERMINING THE POSITION OF A REMOTE OBJECT

TECHNICAL FIELD

The invention relates to the use of magnetic fields for determining the position of remote objects. More particularly, the invention relates to systems and methods for determining the position of a remote object having a magnetic field by using magnetic field spatial geometry characterization point analysis derived from externally sensed magnetic field data.

BACKGROUND OF THE INVENTION

Ingestible wireless medical capsules are known in the medical arts. Such capsules telemetrically transmit information to a receiving and recording apparatus located outside the body. The wireless capsule is swallowed and travels through the digestive tract, collecting and transmitting data during the course of its journey. Receiving and recording apparatus is stationed external to the body. In general, after a day or two, the disposable capsule is excreted naturally from the body and the recorded data, such as for example, temperature, pH, pressure, and transit time, may be transferred for analysis and/or storage. It is known in the art to use wireless medical capsules for collecting images by equipping them with cameras, or for delivering doses of medication to general areas of the digestive system by equipping them with drug reservoirs.

The deployment and detection of relatively small probes or sensors for reconnaissance in confined, inaccessible, or remote spaces is useful in many contexts. Determining the position of an object during deployment faces may challenges. In many applications, the target environment may be no more than a few liters in volume. It is sometimes desirable to determine the position of an object, such as a probe or sensor capsule. with as much precision as possible. Remote sensing may be used in many endeavors, such as industrial or medical applications. For example, the currently available wireless capsules used in the medical field are carried by peristalsis through the digestive tract, and the capsule location during the journey is either unknown or only approximately known. Similarly, in non-medical applications, a probe capsule may be carried by fluid flow and/or gravity, through a system of piping or tubing for example, and its position at any given time only approximated. The lack of position information is a drawback of current wireless capsule technology. For example, often a doctor reviewing data from an in vivo capsule does not know the precise location of features indicated by the data, e.g., an image of a gastrointestinal tumor. Often an additional scoping procedure or even surgery may be required in order to determine the exact location of the problem. In connection with medical devices, some development of magnetic locating techniques has occurred. One approach, exemplified by U.S. Pat. No. 5,558,091 to Acker, is to embed a magnetic sensor in an in vivo capsule, and track the sensor within the body by relating it to magnetic fields external to the body. Although this approach may be useful to some degree, it does not take into account the effect of the earth's magnetic field or the potential interference of additional magnetic fields such as those which may emanate from electrical current and ferromagnetic materials nearby. Another approach, exemplified by U.S. Pat. No. 6,216,028 to Haynor, is to place a magnet on a medical device such as the tip of a probe inserted into the patient, and detect the magnet's field distribution with sensors located on an outside surface of the body. This approach proposes using four magnetic sensors to measure the magnetic field in the x, y, and z axes, and modeling the magnetic tip as a dipole, solving a number of nonlinear equations to determine the position of the magnetic dipole. The complexity of the computations involved require considerable computing power and/or a significant amount of time to complete. The complexity of this approach also increases the potential for considerable error.

Improved systems and methods for accurately determining the position of a remote object, such as a locatable wireless capsule or probe would be useful and advantageous in order to accurately match a location with remotely detected images or other parameters such as pH, temperature, pressure values and so forth. It may also provide advantages for accurately guiding the delivery of medications, or for taking biopsies, or for later surgery. In non-medical applications, it may be used for inspecting piping or fluid-handling systems. Used in conjunction with capsules or probes capable of controlled movement, the capability for timely detection of the probe or capsule position would be particularly advantageous. Due to the foregoing and other problems and potential advantages, improved position determining methods and systems using magnetic fields would a useful contribution to the applicable arts.

SUMMARY OF THE INVENTION

In carrying out the principles of the present invention, in accordance with preferred embodiments, the invention provides advances in the arts with novel methods and apparatus directed to detecting and determining the position of a remote object, such as a capsule or probe, deployed within a target area by sensing its magnetic field in one or more planes. The invention may be used with objects, including but not limited to capsules and probes interchangeably, provided that the tracked object includes a permanent or electrical magnet. Thus, the terms capsule and probe are used interchangeably herein unless noted.

According to one aspect of the invention, a system for determining the position of a remote object includes a targeted object including its own magnetic field for placement on site, i.e., in situ. The system also includes an external magnetic sensor array configured for sensing the magnetic field of the object, e.g., capsule or probe for example, in one or more planes. Computing apparatus is used for magnetic field spatial geometry characterization point analysis in order to determine the position of the object from the sensed magnetic field.

According to another aspect of the invention, a system for determining the position of a remote object as exemplified in the above embodiment also includes at least one background offset sensor for correcting position data for locally measured magnetic fields.

According to another aspect of the invention, a system for determining the position of a remote object as described herein further includes at least one non-stationary sensor plane.

According to yet another aspect of the invention, an in vivo position determining system for medical use includes a capsule or probe having a magnetic field for placement in vivo. The system also includes, deployed outside the body, an external magnetic sensor array configured for sensing the magnetic field of the capsule in one or more planes, as well as magnetic field spatial geometry characterization point analysis apparatus for determining the position of the capsule in vivo from the sensed magnetic field.

According to another aspect of the invention, a preferred embodiment of a method for determining the position of a remote object includes steps for positioning an external magnetic sensor array for sensing the magnetic field of an object within a target area, and using the sensed magnetic field of the object, determining object position data using magnetic field spatial geometry characterization point analysis.

According to another aspect of the invention, an in vivo position determination method includes the step of placing a capsule comprising a magnetic field within a patient, or in vivo. In further steps, an external magnetic sensor array is located for sensing the magnetic field of the capsule. Using the sensed magnetic field, capsule position data is computed by magnetic field spatial geometry characterization point analysis.

The invention has advantages including but not limited to providing one or more of the following; computationally efficient remote position calculation, improved positioning accuracy, and relatively rapid position determination. These and other advantageous, features, and benefits of the invention can be understood by one of ordinary skill in the arts upon careful consideration of the detailed description of representative embodiments of the invention in connection with the accompanying drawings.

BRIEF DESCRIPTION OF THE DRAWINGS

The present invention will be more clearly understood from consideration of the description and drawings in which.

References in the detailed description correspond to like references in the various drawings unless otherwise noted. Descriptive and directional terms used in the written description such as front, back, top, bottom, upper, side, et cetera, refer to the drawings themselves as laid out on the paper and not to physical limitations of the invention unless specifically noted. The drawings are not to scale, and some features of embodiments shown and discussed are simplified or amplified for illustrating principles and features as well as advantages of the invention.

DESCRIPTION OF PREFERRED EMBODIMENTS

While the making and using of various exemplary embodiments of the invention are discussed herein, it should be appreciated that the systems and methods exemplify inventive concepts which can be embodied in a wide variety of specific contexts. It should be understood that the invention may be practiced in various applications and embodiments without altering the principles of the invention. For purposes of clarity, detailed descriptions of functions, components, and systems familiar to those skilled in the applicable arts are not included. In general, the invention provides systems and methods for determining the position of a remote object, for example, an encapsulated probe such as an in vivo medical device, or a probe deployed within a fluid-handling system of piping or tubing. The invention is described in the context of representative example embodiments. Although variations on the details of the embodiments are possible, each has advantages over the prior art due at least in part to increased efficiency realized by performing fewer and/or less complex computations.

Figure 1:
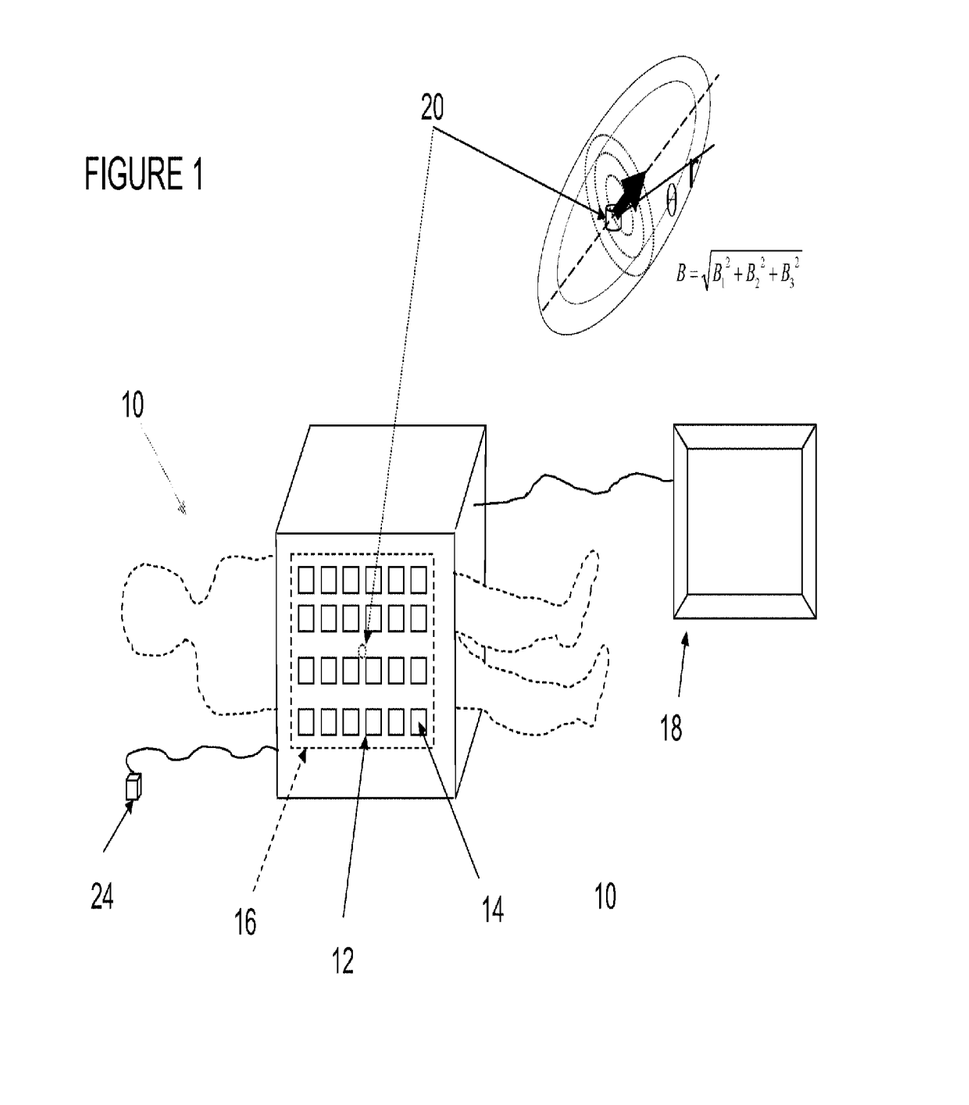
FIG. 1 is a conceptual block diagram providing an overview of systems and methods for determining the position of a remote capsule.

An exemplary embodiment of a system and method for remotely determining the position of an object is shown in the conceptual view of FIG. 1. An operating environment 10 (not part of the invention), such as a medical patient or a confined area such as a mechanical, fluid-handling, or hydraulic system, and at least one sensor array 12 are positioned relative to one another in a configuration further described herein. The sensor array(s) 12 include one or more individual sensor cells 14, preferably uniformly distributed in a sensor plane corresponding with a target area 16 of the operating environment 10. A suitable computer or data processing apparatus 18 is operably coupled to the sensor arrays 12 for performing computations referenced and described herein. A capsule 20, or probe, is preferably deployed inside the target area 16. In the case of a medical implementation, the device may be swallowed by a human or inserted into a veterinary patient, for example. In other implementations, the capsule may be introduced into a system of pipes, a tank or other vessel, mechanical enclosure, or other confined or inhospitable environment where remote sensing or probing is desirable. The capsule 20 includes a dipole magnetic field, preferably generated by a permanent magnet included as a part of the capsule, represented by the diagram inset, and further described by Equation 1. The dipole magnetic field B, is a scalar value (not a vector) wherein m represents the magnetic moment of the magnetic dipole (for the purposes of this description, capsule 20), and wherein r represents distance from the magnetic dipole 20. Angle θ represents the orientation of the capsule 20 relative to moment and distance. It should be appreciated that the capsule 20 typically also includes devices for gathering one or more data points from its surroundings, such as temperature, pH, pressure, chemistry, charge, imagery, and so forth.

$$B(r, \theta) = \frac{\mu_0 m}{4\pi r^3} \sqrt{1 + 3\cos^2\theta} \qquad \text{(Equation 1)}$$

Examples of magnetic field sensor cells 14 include Hall effect sensors, which vary their output voltage responsive to changes in magnetic field, and magneto resistive sensors, which vary their electrical resistance in response to an external magnetic field. The Hall sensor is capable of a greater detection range, whereas magneto resistive sensors are capable of greater sensitivity. Other magnetic sensor types or combinations of sensors may also be used without departure from the invention. A sensor array 12, as shown in the example of FIG. 1, preferably includes multiple sensors in a planar arrangement. Suitable field magnetic sensors on the order of 2 mm×2 mm are commercially available and are presently preferred for in vivo system embodiments. For example, in an array of 2 mm magnetic filed sensors spaced 5 mm apart, when the detected magnetic field is 0.01 Gauss, using the systems and methods further described herein, a spatial resolution of 0.5 mm is attainable. Accordingly, the position of the magnetic field, e.g., magnetic dipole or capsule 20 location, may be determined within about 1 mm. In order to scan a target area larger than the sensor array, and/or to reduce the number of sensor cells required in an array, the sensor array may be moved relative to the target area, or vice versa. The magnetic sensor array and/or target area movement is preferably conducted along the plane described by the sensor array, preferably using a mechanical guide to ensure that the correct orientation is maintained and automated or human impelling force.

Preferably, positioning accuracy is enhanced by taking into account an offset magnetic field value when performing positioning computations described herein. A value for the earth's magnetic field, for example, may be stored and applied for correction of calculations made based on magnetic field sensor values indicative of the position of the capsule. Additionally, or alternatively, a magnetic field offset sensor 24 may be used to provide an actual offset value for the particular location and conditions, e.g. the earth magnetic field and the presence of magnetic materials or field-generating electric current. The capsule position data is preferably corrected using the magnetic field offset data. The magnetic field offset sensor 24 is preferably positioned so that it will not sense the magnetic field of the capsule 20, and bears a known, preferably constant, spatial relationship to the magnetic field sensor cells 14 of the magnetic field sensor array 12.

Figure 2:
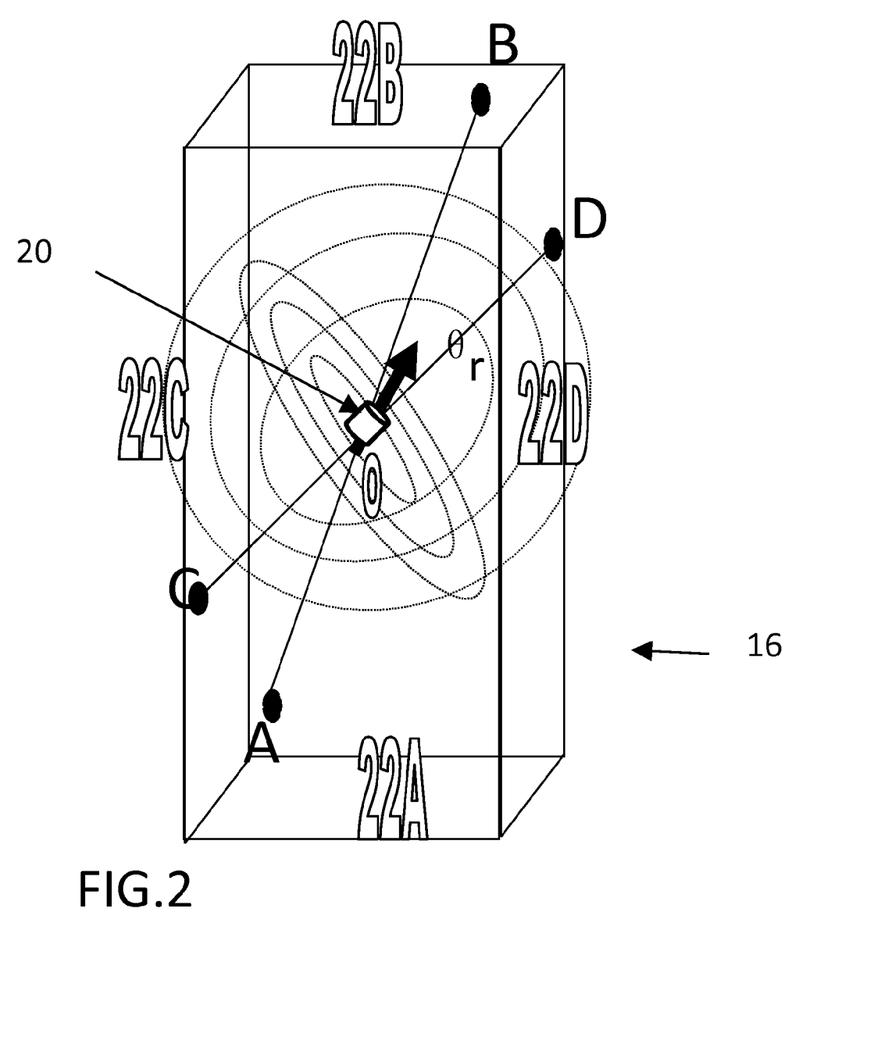
FIG. 2 depicts an example of a preferred embodiment of a position determination system and method in which four magnetic field sensor planes are used.

Now referring primarily to FIG. 2, a preferred embodiment of a system and method is shown, in which a target area 16 is encompassed within four magnetic field sensor planes, denominated 22A, 22B, 22C, and 22D. Preferably, the sensor planes are configured in sets of two parallel planes. As shown in FIG. 2, front plane 22A is parallel to back plane 22B, and left plane 22C is parallel to right plane 22D. Preferably, the maximum magnetic field point is determined by magnetic field sensor readings on each plane, indicated in FIG. 2 by points A, B, C, and D, respectively. The maximum points on the opposing planes are used to define lines AB and CD. The intersection of the lines indicates the point O within the target area 16 at which the magnetic field is strongest, thus giving the capsule 20 position in three-dimensional space. Preferably, a magnetic field offset is applied to correct the position information based on what is known about magnetic fields present in the operating environment, such as the earth's magnetic field and/or additional locally detected magnetic fields. Those skilled in the arts should note that this particular embodiment does not require data concerning the magnetic field direction; no magnetic moment value is needed. The method and system described in this embodiment offers advantages in efficiency, requiring reduced computation and processing time, and/or reduced complexity relative to the prior art.

Figure 3:
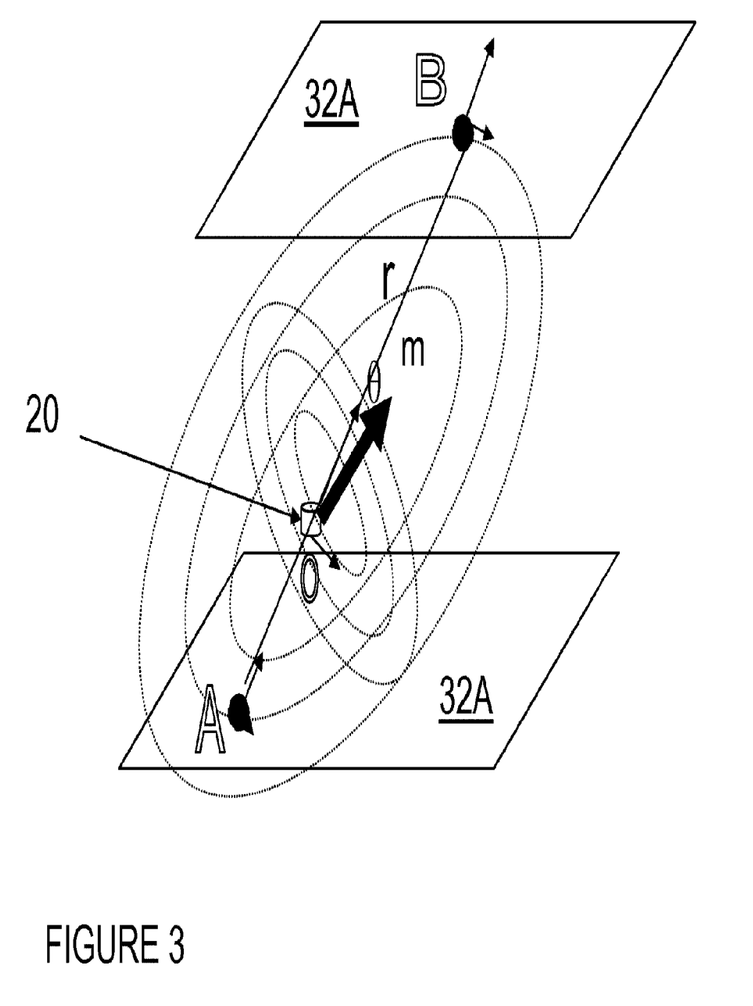
FIG. 3 illustrates an example of an alternative preferred embodiment of a position determination system and method in which two magnetic field sensor planes are used.

In another preferred embodiment, illustrated in FIG. 3, the position of the capsule 20 may be determined using two sensor planes, denoted 32A and 32B. The sensor planes 32A, 32B, are preferably parallel. The maximum magnetic field points, A, B, and the magnetic field vector are used to determine the dipole location O and orientation. Referring to Equations 2-7, the moment of the magnetic dipole is related to the magnetic field. The dipole magnetic moment m is derived from the dipole moment along line AB and perpendicular to line AB. (Equations 1-2). The magnetic field at point A can be derived from the magnetic field along line AB, and perpendicular to line AB. The same can be done for point B. The magnetic fields of the dipole are preferably computed as shown in Equations 3 and 4. Since the magnetic fields along the x, y, and z axes are measured at the magnetic field sensor cells, the line AB perpendicular and parallel component values can be calculated with the measurement data. Thus the dipole position, point O, can be calculated (Equation 5), and the angle θ can be derived. (Equation 6). The dipole's perpendicular orientation is the same as the line AB perpendicular magnetic field component, thus the dipole orientation can also be determined. It should be noted that the two parallel planes may alternatively be located on the same side of the dipole without departure from the invention, since the line between their maximum points, e.g., line AB, would nevertheless be established.

$$\vec{m} = \vec{m}_{AB\parallel} + \vec{m}_{AB\perp} \quad \text{(Eq. 2)}$$

$$m_{AB\parallel} = m\cos\theta, \; m_{AB\perp} = m\sin\theta \quad \text{(Eq. 3)}$$

$$B_{A\_AB\parallel} = \frac{\mu_0 m_{AB\parallel}}{2\pi r_{OA}^3}, \; B_{B\_AB\parallel} = \frac{\mu_0 m_{AB\parallel}}{2\pi r_{OB}^3} \quad \text{(Eq. 4)}$$

$$B_{A\_AB\perp} = \frac{\mu_0 m_{AB\perp}}{4\pi r_{OA}^3}, \; B_{B\_AB\perp} = \frac{\mu_0 m_{AB\perp}}{4\pi r_{OB}^3} \quad \text{(Eq. 5)}$$

$$\frac{OA}{OB} = \sqrt[3]{\frac{B_{A\_AB\parallel}}{B_{B\_AB\parallel}}} = \sqrt[3]{\frac{B_{A\_AB\perp}}{B_{B\_AB\perp}}} \quad \text{(Eq. 6)}$$

$$\tan\theta = \frac{B_{A\_AB\perp}}{2B_{A\_AB\parallel}} = \frac{B_{B\_AB\perp}}{2B_{B\_AB\parallel}} \quad \text{(Eq. 7)}$$

Figure 4:
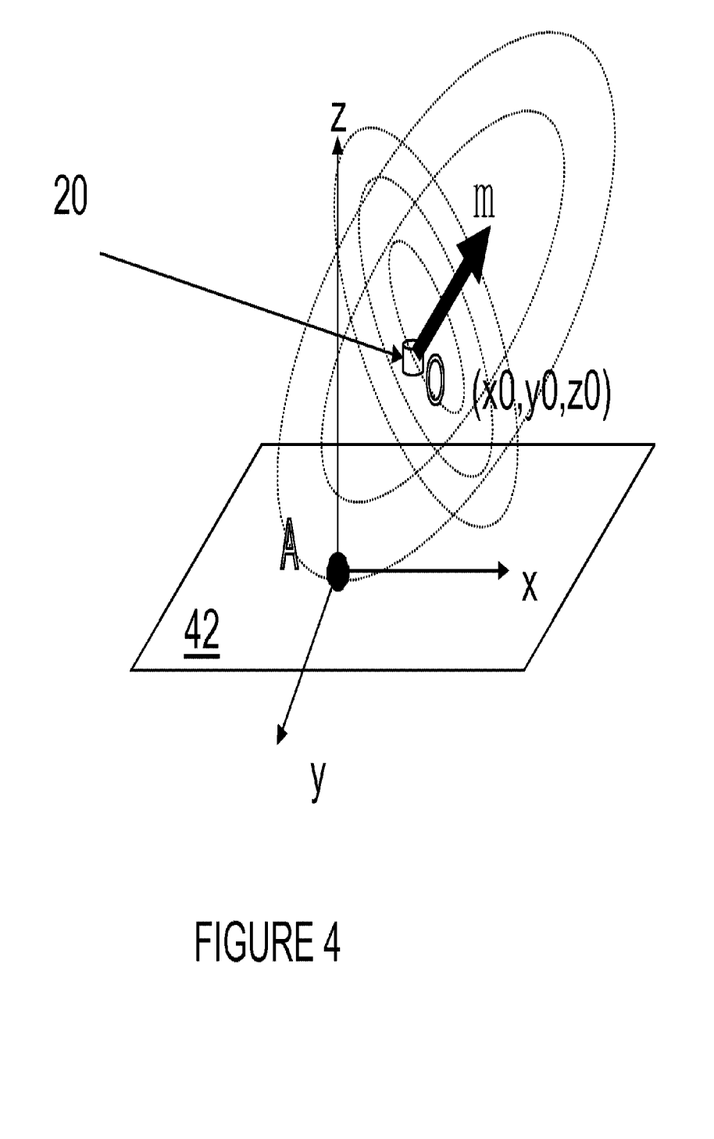
FIG. 4 provides an example of an alternative preferred embodiment of a position determination system and method in which a single magnetic field sensor plane is used.

In an example of an alternative embodiment of the invention, depicted in FIG. 4, a single magnetic field sensor plane 42 is used to determine the position of the magnetic field of a capsule 20. By the partial differentiation of the magnetic field curve, the maximum field condition is derived. The set of the nonlinear equations, Equations 8-11.6, express the derivation of the dipole location and orientation from the sensed magnetic field.

$$B(x, y, z) = \sqrt{B_x^2 + B_y^2 + B_z^2} = \frac{\mu_0}{4\pi}\frac{1}{r^4}\sqrt{3Q^2 + m^2 r^2} \quad \text{(Eq. 8)}$$

$$Q = [m_x(x - x_0) + m_y(y - y_0) + m_z(z - z_0)]$$

$$r = \sqrt{(x - x_0)^2 + (y - y_0)^2 + (z - z_0)^2}$$

$$F(x, y, z) = \frac{\mu_0}{4\pi}\frac{1}{r^4}\sqrt{3Q^2 + m^2 r^2} - B \quad \text{(Eq. 9)}$$

$$\left(\frac{\partial F}{\partial x}, \frac{\partial F}{\partial y}, \frac{\partial F}{\partial z}\right) \quad \text{(Eq. 10)}$$

$$\frac{\partial F}{\partial x} = 0, \quad \text{(Eq. 11.1)}$$

$$\frac{\partial F}{\partial y} = 0, \quad \text{(Eq. 11.2)}$$

$$\frac{\partial F}{\partial z} = 1 \quad \text{(Eq. 11.3)}$$

$$B_x = \frac{\mu_0}{4\pi}\frac{3Q(x - x_0) - m_x r^2}{r^5} \quad \text{(Eq. 11.4)}$$

$$B_y = \frac{\mu_0}{4\pi}\frac{3Q(y - y_0) - m_y r^2}{r^5} \quad \text{(Eq. 11.5)}$$

$$B_z = \frac{\mu_0}{4\pi}\frac{3Q(z - z_0) - m_z r^2}{r^5} \quad \text{(Eq. 11.6)}$$

Assuming for example, that the maximum magnetic field is at point A (0, 0, 0). The equal magnetic field curve Q has a tangent plane (z=0) at A, and the normal line is vector (0, 0, 1). The magnetic field, B(x, y, z) is as shown by Equation 8. The curve Q equation is as represented by Equation 9. The vector of the curve surface is shown by Equation 10. Considering the normal line at the tangent plane at point A permits the derivation of six equations (Equations 11.1-11.6), which can be used to solve for the six unknown parameters, denoted, x0, y0, z0, mx, my, and mz, that represent the magnetic dipole location O, in this case coinciding with capsule 20, position and orientation.

Figure 5A:
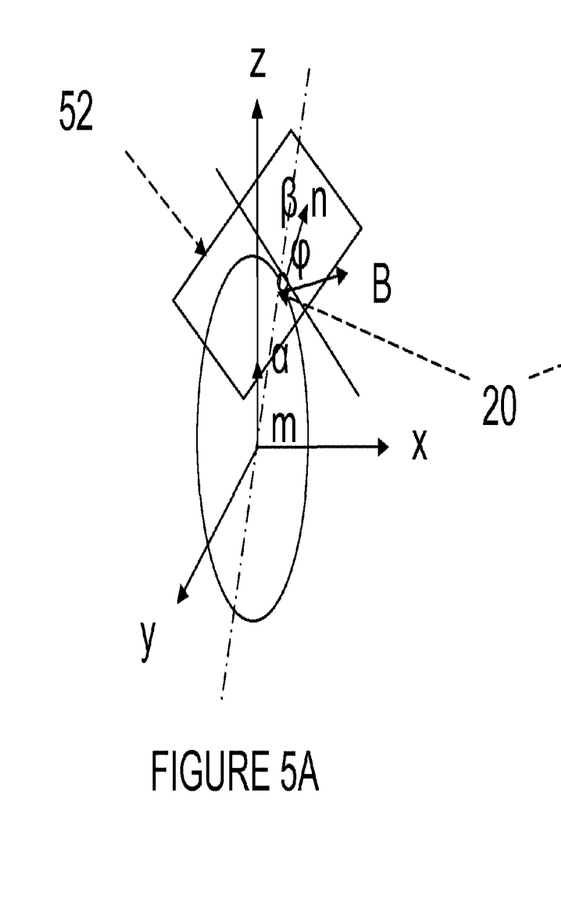
FIGS. 5A and 5B show an example of an additional alternative preferred embodiment of a position determination system and method in which a single magnetic field sensor plane is employed.
Figure 5B:
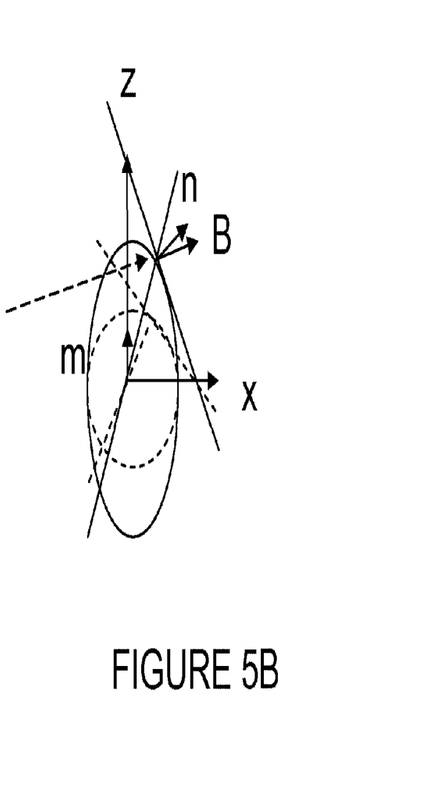

In another example of an alternative embodiment of the invention, illustrated using FIGS. 5A and 5B, a single magnetic field sensor plane 52 is used to determine the position of the magnetic field. In this method the magnetic moment is used to provide a simpler and faster approach for solving the nonlinear equation set (Equations 8-11.6). It should be appreciated that this approach may also be combined with the above method, eliminating the requirement that the magnetic moment value first be known.

$$B\cos(\beta + \varphi) = \frac{\mu_0}{4\pi} \frac{2m\cos\alpha}{r^3} \qquad \text{(Eq. 12.1)}$$

$$B\sin(\beta + \varphi) = \frac{\mu_0}{4\pi} \frac{m\sin\alpha}{r^3} \qquad \text{(Eq. 12.2)}$$

$$tg(\beta + \varphi) = 2tg\alpha \qquad \text{(Eq. 12.3)}$$

$$tg(\beta + \alpha) = 2^{2/3} tg\alpha \qquad \text{(Eq. 12.4)}$$

Assuming for the sake of example that the magnetic dipole is at (0, 0, 0) oriented along the z-axis; The normal line n is perpendicular to the tangent plane at the measured B maximum. By geometric symmetry, the maximum field vector B and the normal vector n, and the dipole moment vector m, are in the same plane. This effectively reduces the three dimensional positioning problem to a two dimensional problem. The angle $\phi$ between the B vector and n vector is known from sensor data. In order to solve the problem, $\alpha$ and $\beta$ are first determined. Evaluating the maximum magnetic field vector and dipole moment vector, shown along the connecting dashed line in FIG. 5A, the relationships are calculated using Equations 12.1 and 12.2. The first angle equations are derived (Equations 12.3 and 12.4) in accordance with the topology change as shown in FIG. 5B. The space defined by the dashed line shown is a linear geometry transform from the solid taken along the z direction. From the dipole field equation, transferring the z scale with about $\sqrt[3]{\sqrt{2}}$ the curve surface may be described as a sphere, but the topology characteristics are maintained, such as the tangent points. Given the geometric relationships of the points, using Equations 12.3-12.4, $\alpha$ and $\beta$ can be found, determining the dipole orientation. If the magnetic moment m is known, using Equation 8 or 9, the distance R is determined, representing the magnetic dipole location 20. Computationally, this method is simpler relative to alternatives, providing advantages in efficiency, particularly for making time-sensitive position determinations, such as, for example in systems equipped for real-time sensing and/or controlled movement of a capsule or probe.

The systems and methods of the invention provide one or more advantages including but not limited to, providing accurate position determination for remote objects using measurements and analysis based on magnetic fields, increased efficiency, reduced costs. While the invention has been described with reference to certain illustrative embodiments, those described herein are not intended to be construed in a limiting sense. For example, variations or combinations of steps or materials in the embodiments shown and described may be used in particular cases without departure from the invention. Although the presently preferred embodiments are described herein in terms or planes and planar geometry, it is possible to practice the invention by substituting curved surfaces for planes, and adapting the calculations based on the selected curvature. Also, the computations described in terms of maximum values may be adapted to use minimum values or selected intermediate values without departure from the principles of the invention. These and other modifications and combinations of the illustrative embodiments as well as other advantages and embodiments of the invention will be apparent to persons skilled in the arts upon reference to the drawings, description, and claims.

We claim:

1. A method of measuring a magnetic dipole by using spatial geometry characterization, the method comprising:
    determining position data (of point O) and orientation of the magnetic dipole, comprising removing background magnetic field in a target area;
    placing an object having a permanent magnetic dipole in the target area;
    sensing a magnetic field of the object using a plurality of magnetic sensors distributed on two sensor planes, wherein a first sensor plane is opposite to a second sensor plane, and the first and the second sensor planes are parallel to each other;
    identifying position points (A and B) of a maximum magnetic field of the object on the two sensor planes; and
    deriving a position of the object by solving Equation 6 (Eq.6) and Equation 7 (Eq.7):

$$\frac{OA}{OB} = \sqrt[3]{\frac{B_{A\_AB\|}}{B_{B\_AB\|}}} = \sqrt[3]{\frac{B_{A\_AB\perp}}{B_{B\_AB\perp}}} \qquad \text{(Eq. 6)}$$

$$\tan\theta = \frac{B_{A\_AB\perp}}{2B_{A\_AB\|}} = \frac{B_{B\_AB\perp}}{2B_{B\_AB\|}} \qquad \text{(Eq. 7)}$$

wherein
    OA is a distance from point O to point A;
    OB is a distance from point O to point B;
    $B_{A\_AB\|}$ is a dipole generated magnetic field component at point A, and said component is in a direction parallel to a line connecting point A to point B;
    $B_{B\_AB\|}$ is a dipole generated magnetic field component at point B, and said component is in the direction parallel to the line connecting point A to point B;
    $B_{A\_AB\perp}$ is a dipole generated magnetic field component at point A, and said component is in a direction perpendicular to the line connecting point A to point B;
    $B_{B\_AB\perp}$ is a dipole generated magnetic field component at point B, and said component is in the direction perpendicular to the line connecting point A to point B; and
    $\theta$ is an angle between a position vector of a field measurement at point O and the line connecting point A to point B.

2. The method of claim 1, further comprising identifying the orientation of the magnetic dipole.

3. The method of claim 1, wherein at least one sensor on the sensor plane is a member of a sensor array.

4. The method of claim 3, wherein the sensor array further comprises
    at least one Hall sensor.

5. The method of claim 3, wherein the sensor array further comprises
    at least one magneto resistive sensor.

6. The method of claim 1, wherein the magnetic sensors on the two sensor planes sense the magnetic field simultaneously.

7. The method of claim 1, wherein the two sensor planes are positioned on opposite sides of the object.

8. The method of claim 1, wherein the target area comprises an in vivo area.

9. A method of measuring a magnetic dipole by using spatial geometry characterization, the method comprising:
- determining position data and orientation of the magnetic dipole, comprising removing background magnetic field in a target area;
- placing an object having a permanent magnetic dipole in the target area;
- sensing a magnetic field of the object using one magnetic sensor plane,
- measuring a position point (A) and value B of a maximum magnetic field on said sensor plane; and
- calculating a location of the object by solving equations 12.1-12.4

$$B\cos(\beta + \varphi) = \frac{\mu_0}{4\pi} \frac{2m\cos\alpha}{r^3} \quad \text{(Eq. 12.1)}$$

$$B\sin(\beta + \varphi) = \frac{\mu_0}{4\pi} \frac{m\sin\alpha}{r^3} \quad \text{(Eq. 12.2)}$$

$$tg(\beta + \varphi) = 2tg\alpha \quad \text{(Eq. 12.3)}$$

$$tg(\beta + \alpha) = 2^{2/3} tg\alpha \quad \text{(Eq. 12.4)}$$

wherein
- B is a maximum dipole magnetic field value at the magnetic sensor plane;
- $\beta$ is an angle between a normal vector of the magnetic sensor plane, and a line connecting a maximum dipole magnetic field value position and a magnetic dipole position;
- $\alpha$ is an angle between a dipole magnet moment vector, and the line connecting the maximum dipole magnetic field value position and the magnetic dipole position;
- $\varphi$ is an angle between the normal vector of the magnetic sensor plane and a dipole magnetic field vector direction at the maximum dipole magnetic field value position;
- m is a magnetic moment value of the magnet dipole;
- r is a distance between the magnet dipole position and the maximum dipole magnetic field value position in the magnetic sensor plane; and
- $\mu_0$ is a permeability of a vacuum.

10. The method of claim 9, further comprising using a geometry symmetry method to reduce three dimension analysis into a two dimension analysis.

11. The method of claim 9, further comprising decomposing the value of maximum magnetic field into a component in the sensor plane.

12. The method of claim 9, wherein the target area comprises an in vivo area.

\* \* \* \* \*